United States Patent [19]

Mendler

[11] Patent Number: 5,658,136
[45] Date of Patent: Aug. 19, 1997

[54] CENTRIFUGAL BLOOD PUMP

[75] Inventor: Nikolaus Mendler, Berg, Germany

[73] Assignee: Jostra Medizintechnik GmbH, Hirrlingen, Germany

[21] Appl. No.: 502,093

[22] Filed: Jul. 13, 1995

[30] Foreign Application Priority Data

Aug. 31, 1994 [DE] Germany .................. 44 30 853.1

[51] Int. Cl.[6] .................................................. F04D 29/00
[52] U.S. Cl. .................................................. 417/420
[58] Field of Search .......................... 415/122.1, 123, 415/124.2, 900; 417/420

[56] References Cited

U.S. PATENT DOCUMENTS

| 3,647,324 | 3/1972 | Rafferty et al. | 417/420 |
|---|---|---|---|
| 4,135,863 | 1/1979 | Davis et al. | 417/420 |
| 4,779,614 | 10/1988 | Moise | 600/16 |
| 4,984,972 | 1/1991 | Clausen et al. | 417/420 X |
| 5,017,103 | 5/1991 | Dahl | 417/420 |
| 5,174,726 | 12/1992 | Findlay . | |
| 5,316,440 | 5/1994 | Kijima et al. | 415/900 |
| 5,385,581 | 1/1995 | Bramm et al. | 417/356 |

FOREIGN PATENT DOCUMENTS

| 393456 | 11/1989 | Austria . |
| 3133177 | 8/1981 | Germany . |
| 1383811 | 1/1972 | United Kingdom . |

*Primary Examiner*—John T. Kwon
*Attorney, Agent, or Firm*—Michael J. Striker

[57] ABSTRACT

The centrifugal blood pump has a pump rotor (15) arranged inside a housing (13) which is closed with the exception of a blood outlet (15') and a blood inlet (14). The rotatable pump rotor (15) inside the housing (13) is driven by an external drive motor (10) via a magnetic coupling. The magnetic coupling is provided by thin exterior permanent magnets (21) circumferentially distributed around the rotor (15) on a coupling part (12,20) connected to the external drive motor (10) and correspondingly thin circumferentially distributed permanently magnetized ferromagnetic regions (17,18) of the pump rotor which are coupled with the permanent magnets (21) to form a magnetic field bridge (22) and thus to avoid axially directed tilting or tipping moments. The pump rotor (15) can be additionally stabilized against translational motion in the radial direction by a mechanical bearing device (24) for the rotor which is provided inside an interior space through which blood flows in the pump housing.

10 Claims, 2 Drawing Sheets

CENTRIFUGAL BLOOD PUMP

BACKGROUND OF THE INVENTION

The present invention relates to a centrifugal blood pump, especially for a heart substitute device.

A centrifugal blood pump is known comprising a housing having at least one blood outlet and at least one blood inlet which is closed in a liquid and gas-tight manner except at the blood outlets and inlets and a rotatable pump rotor arranged in the housing, which is driven by an external drive motor located outside of the housing by means of a magnetic coupling.

Centrifugal blood pumps are becoming more important than the so-called roller pumps and also the ventricular pumps for feeding blood, since the disadvantages of these latter blood pumps can be avoided with them. With the easy-to-operate and economical roller pumps these disadvantages include an insensitivity to the medium being pumped, since roller pumps are pure displacement pumps so that, when a connected blood reservoir is empty, air could be pumped into a patient from it with fatal consequences. Furthermore an arbitrarily higher pressure can build up in the system if the blood flow is blocked. Because of the continuous pressing action of the roller on a blood feed tube mechanical hemolysis is unavoidable and an embolytic danger of significant abrasion in the inside of the tube results.

The main disadvantage to the ventrical pump, besides the possible feeding of air, is that its construction is difficult because of its membranes and valves so that it is correspondingly expensive and thus is not suitable for a one-way device required by safety considerations.

In contrast the centrifugal blood pump has the advantage that pumping action is immediately interrupted during a large air inflow. Also mechanical abrasion of plastic particles and their spreading into the blood stream need not be taken into consideration. Blood damage by rotary pumps is noticeably less than by roller pumps. The centrifugal pumps known up to now used for feeding blood in extracorporeal circulation have however always had the disadvantage that they are expensive to construction, also pump parts used in their construction are articles which can be used only once. Bearings are provided for the rotor outside of the blood conducting regions of the pump, which must be sealed by shaft packing from the blood conducting regions. Additional disadvantages include a disadvantageous loss by frictional heat dissipation, which can lead to a local overheating of blood with a danger of denaturation of blood cell proteins and cell destruction during longer dwell times of blood in the pump. Of course seal-less centrifugal blood pumps and with bearing-less rotors with exclusively magnetic stabilization have already been proposed. These pumps still have the disadvantage of a comparatively large construction expense and expensive control means with electromagnetic feedback based on stability considerations and thus an undesirably large pump rotor, which leads again to a large blood chamber volume with correspondingly larger frictional contact surfaces for the blood and a comparatively longer dwell time of the blood in the pump regions.

SUMMARY OF THE INVENTION

It is an object of the present invention to provide a centrifugal blood pump of the above-described type having a satisfactory compact structural form made from its pump parts as a one-time or one-use article, which avoids the above-described disadvantages.

According to the invention the centrifugal blood pump comprises a housing provided with at least one blood outlet and at least one blood inlet and closed in a liquid and gas-tight manner except at the at least one blood outlet and at least one blood inlet, a rotatable pump rotor arranged inside the housing and provided with ferromagnetic regions distributed uniformly around a circumference of the pump rotor, an external drive motor outside the housing and having means for magnetic coupling of the pump rotor and the drive motor. The means for magnetic coupling of the pump rotor and the drive motor include a rotational coupling part arranged outside of the housing and permanent magnets distributed uniformly around a circumference of the rotational coupling part so that the pump rotor is driven and rotationally stabilized by magnetic action of the permanent magnets mounted on the rotational coupling part outside the housing on the ferromagnetic regions of the pump rotor iniside the housing.

The desired compactness of the pump device is provided primarily by the radially acting magnetic drive coupling of the pump rotor with the external drive device and by avoiding uneconomical and expensive stabilizing magnets in the vicinity of the pump rotor. In a preferred embodiment of the invention an added sleeve bearing for the rotor is provided in the seal-free interior space of the housing through which blood flows. Furthermore the permanently magnetized or nonpermanently magnetized ferromagnetic regions of the pump rotors have a height reduced so that the ratio of the radius of the driven part of the pump rotor to the height of the ferromagnetic regions amounts to at least 10:1. The rotational coupling part connected with a external drive motor and arranged outside the housing appropriately is provided with reduced axial height. The driven part of the pump rotor is appropriately formed like a disk and provided with elements for feeding blood on at least one of the two axial sides of this driven part. Advantageously the same number of permanent magnets are present as ferromagnetic regions.

Experiments with a first prototype have already shown that a centrifugal blood pump according to the invention with a comparatively small pump chamber volume and with its comparatively economical one-way pump parts may be constructed so that the contact surface area of the pump parts which the flowing blood contacts is reduced in comparison to that of the known centrifugal blood pump and the dwell time of the blood in the pump device is substantially shorter than that of the known centrifugal blood pump. The efficiency of the blood pump according to the invention is correspondingly high. No overheating and no noticeable mechanical hemolysis can occur in the high blood throughput due to the pump at the added sleeve bearing, particularly a point bearing. The combination of a good magnetic stabilization in the axial direction with additional mechanical stabilization of the pump rotor in the radial direction produces no disadvantageous compromises, but provides a higher operating reliability in an economical simpler structure in comparison to the expensive purely magnetic stabilization of the rotor of this type of pump. The stabilization of the rotor is not interrupted during a power outage so that the pump can be additionally operated manually.

BRIEF DESCRIPTION OF THE DRAWING

The objects, features and advantages of the present invention will now be illustrated in more detail by the following detailed description, reference being made to the accompanying drawing in which.

DESCRIPTION OF THE PREFERRED EMBODIMENTS

Figure 1:
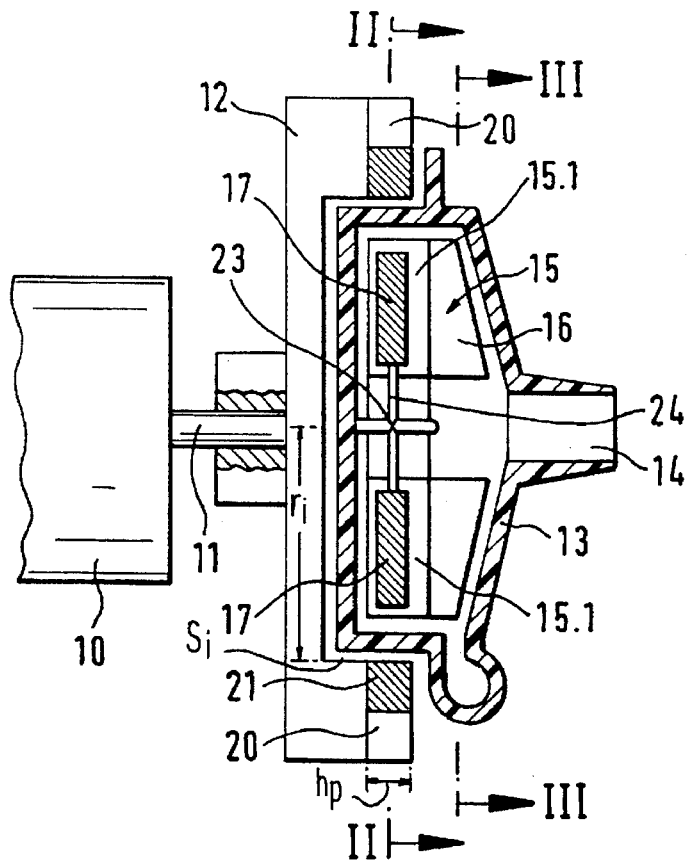
FIG. 1 is a central longitudinal cross-sectional view through a centrifugal blood pump according to the invention.
Figure 3:
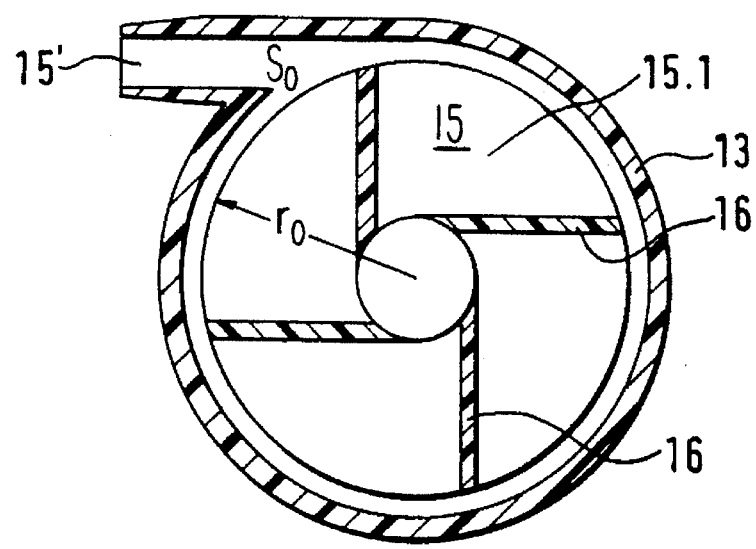
FIG. 3 is a transverse cross-sectional view through the blood pump of FIG. 1 taken along section line III—III of FIG. 1.

FIG. 1 shows an electric drive motor 10, its drive shaft 11, a disk 12 concentrically attached to the drive shaft 11 and a pump housing 13 arranged in a fixed and exchangeable manner in an unillustrated holder. The pump housing 13 is sealed or closed for gases and liquids except at a central pump inlet opening 14 and a tangentially arranged pump outlet opening 15' seen in FIG. 3. The pump housing 13 is an operating part, which is provided only for one-time use, in an unshown extracorporeal section of a blood circulation apparatus.

Figure 2:
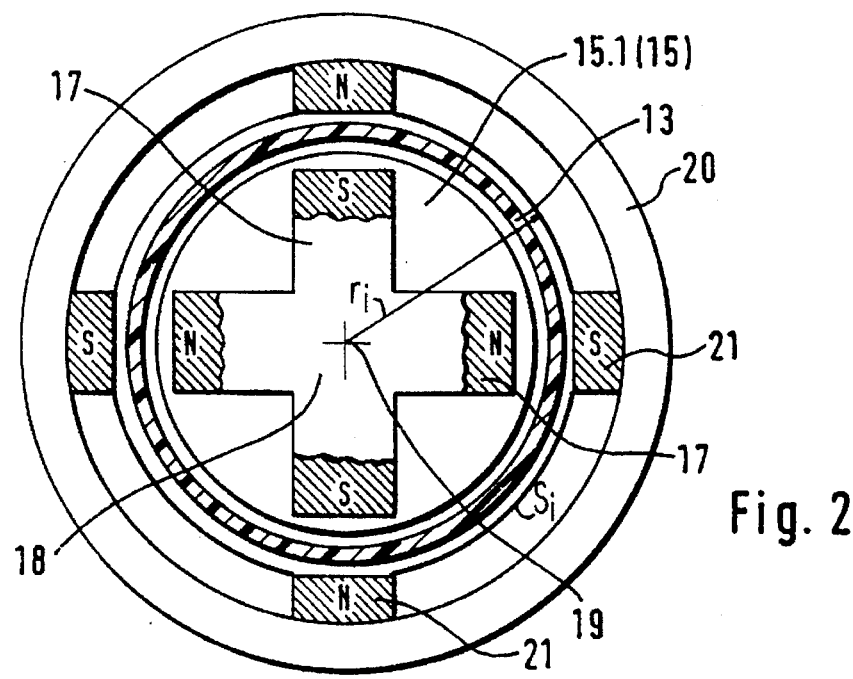
FIG. 2 is a transverse cross-sectional view through the blood pump of FIG. 1 taken along section line II—II of FIG. 1.

A pump rotor 15 is arranged in an interior space inside the sealed pump housing 13, which comprises a disk-like rotor body driven part 15.1. Blade elements 16 are arranged on one axial side of the rotor body driven part 15.1. The blade elements 16 are curved blades of an impeller wheel or device and are shaped in a known way. Ferromagnetic regions 17, which are permanently magnetized in the embodiment shown, are distributed uniformly over the entire circumference of the disk-like rotor body driven part 15.1. As shown in the cross-section of FIG. 2, the ferromagnetic regions 17 in this embodiment are the arms of an equal-armed cross 18, and this ferromagnetic cross 18 is permanently magnetized so that its four arms form north poles N and south poles S following each other alternately in a rotation direction around it. The rotation axis 19 of the pump rotor 15 is coaxial to the drive shaft 11 of the drive motor 10 which is connected with an unshown electrical control device.

A ring 20 surrounding the pump housing 13 is arranged at the axial level of the driven part 15.1 of the pump rotor 15 on the disk 12 connected with the drive shaft 11 of the motor 10. Four permanent magnets 21 are mounted on its interior side in the embodiment according to FIG. 2. These permanent magnets 21 form north poles N and south poles S alternating in a circumferential direction around the pump rotor 15 and its driven part 15.1. The permanent magnets 21 together with the ring 20 extend with constant spacing around the stationary pump housing 13 forming a magnetic ground bridge and thus drive the pump rotor 15 by action of magnetic forces on the ferromagnetic cross 18 of its driven part 15.1. Simultaneously the pump rotor is stabilized in four of six spatial degrees of freedom.

Figure 4:
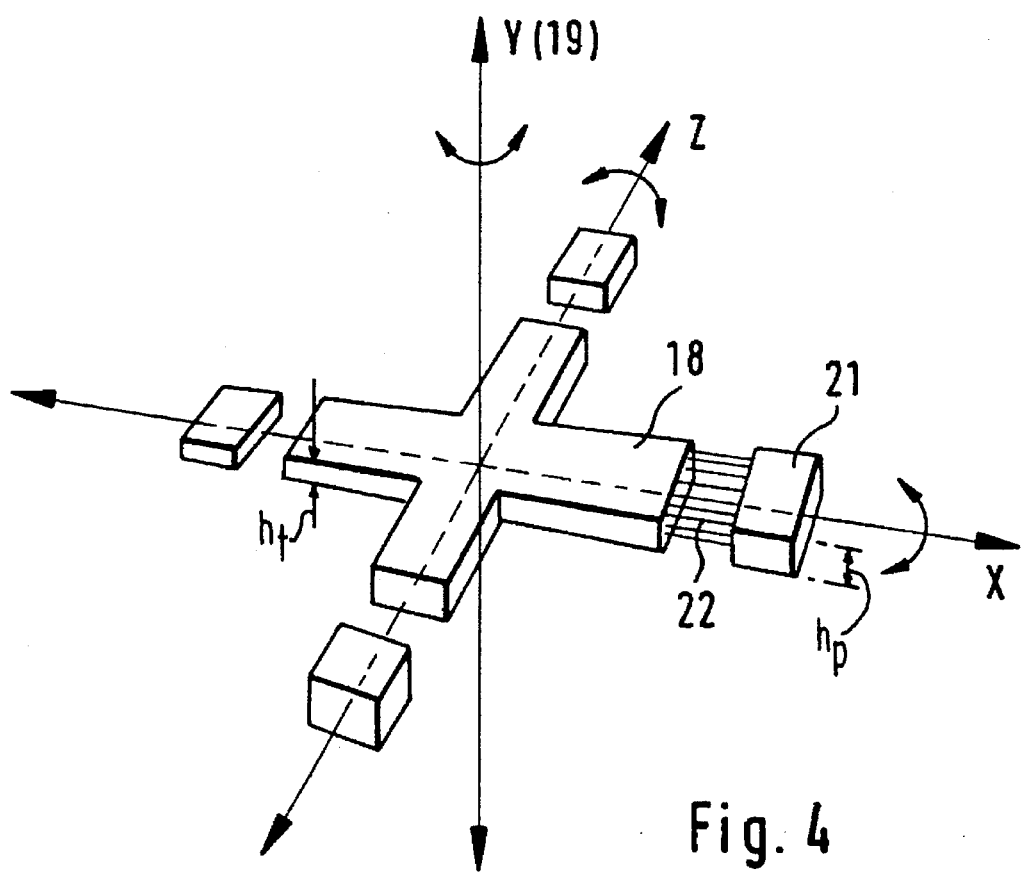
FIG. 4 is a separate perspective view of the magnetic driving and stabilizing systems for the pump rotor.

FIG. 4 shows the principle of magnetic coupling between the rotating permanent magnets 21 and the ferromagnetic cross 18 of the pump rotor diagrammatically. The magnetic coupling causes the rotation of the pump rotor 15 around the rotation axis 19 when the drive motor is operated because the magnetic coupling causes the pump rotor to rotate with the permanent magnets 21. FIG. 4 shows also that the ferromagnetic cross 18 and the rotating permanent magnets 21 are formed as thin plates or platelets, whereby the rotating permanent magnets 21 form a magnetic field bridge 22 to the arms of the ferromagnetic cross 18 which is flat so that because of it no noticeable tilting or tipping moments are applied to the associated arms of the ferromagnetic cross 18. Furthermore a stabilization of the pump rotor occurs by uniform distribution of the magnetic bridges 22 around the circumference of the pump rotors and its ferromagnetic cross 18.

In preferred embodiments as shown in the drawing a rotational coupling part 12,20 comprising the disk 12 and the ring 20 has an inner circumferential surface $S_i$ having a radius $r_i$ extending from a rotation axis 19 of the pump rotor 15 to that inner circumferential surface $S_i$. The pump rotor 15 has an outer circumferential surface $S_o$ having a radius $r_o$ extending from a rotation axis 19 of the pump rotor 15 to said outer circumferential surface $S_o$. The ratio of the radius $r_i$ of the inner circumferential surface $S_i$ of the rotational coupling part 12,20 to the height $h_p$ of the permanent magnets 21 or the height $h_f$ of the ferromagnetic regions 17,18 is at least 10:1. Similarly, the ratio of the radius $r_o$ of the outer circumferential surface $S_o$ of the pump rotor 15 to the height $h_p$ of the permanent magnets 21 or the height $h_f$ of the ferromagnetic regions 17,18 is at least 10:1.

The rotor 15 is quasi-point mounted inside the housing 13 on the centrally positioned bearing tip or post 23 shown in FIG. 1 by means of bearing disk 24 provided with a disk opening having a knife-like edge inspite of its magnetic stabilization in four of six degrees of freedom in the embodiment shown the centrifugal blood pump according to the invention and, because of that, is mechanically stabilized against translational motion in the X-Z plane (FIG. 4).

While the invention has been illustrated and described as embodied in a centrifugal blood pump, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

I claim:

1. Centrifugal blood pump comprising a housing (13) provided with at least one blood outlet (15') and at least one blood inlet (14) and closed in a liquid and gas-tight manner except at the at least one blood outlet (15') and at least one blood inlet (14), a rotatable pump rotor (15) arranged inside the housing (13) and provided with a number of ferromagnetic regions (17,18) distributed uniformly circumferentially in the pump rotor, an external drive motor (10) outside the housing (13) and means for magnetic coupling of the pump rotor (15) and the drive motor (10) to drive the pump rotor (15) rotatably, wherein said means for magnetic coupling of the pump rotor (15) and the drive motor (10) include a rotational coupling part (12,20) attached to the drive motor (10) to be rotatably driven thereby and arranged outside of the housing (13) and a number of permanent magnets (21) distributed uniformly around a circumference of the rotational coupling part (12,20) so that said pump rotor (15) is driven and rotationally stabilized by action of the permanent magnets (21) mounted on the rotational coupling part (12, 20) on the ferromagnetic regions (17,18) of the pump rotor (15), wherein the permanent magnets (21) have a height ($h_p$) in an axial direction of the pump rotor (15) at least approximately equal to a height ($h_f$) of the ferromagnetic regions (17,18) of the pump rotor (15) in the axial direction of the pump rotor.

2. Centrifugal blood pump comprising a housing (13) provided with at least one blood outlet (15') and at least one blood inlet (14) and closed in a liquid and gas-tight manner except at the at least one blood outlet (15') and at least one blood inlet (14), a rotatable pump rotor (15) arranged inside the housing (13) and provided with a number of ferromagnetic regions (17,18) distributed uniformly circumferentially in the pump rotor, an external drive motor (10) outside the housing (13) and means for magnetic coupling of the pump rotor (15) and the drive motor (10) to drive the pump rotor (15) rotatably, wherein said means for magnetic coupling of the pump rotor (15) and the drive motor (10) include a rotational coupling part (12,20) attached to the drive motor (10) to be rotatably driven thereby and arranged outside of the housing (13) and a number of permanent magnets (21) distributed uniformly around a circumference of the rotational coupling part (12,20) so that said pump rotor (15) is driven and rotationally stabilized by action of the permanent magnets (21) mounted on the rotational coupling part (12, 20) on the ferromagnetic regions (17,18) of the pump rotor (15), wherein said rotational coupling part (12,20) has an inner circumferential surface ($S_i$) having a radius ($r_i$), said permanent magnets (21) have a height ($h_p$) in an axial direction of the pump rotor (15) and a ratio of said radius ($r_i$) of said inner circumferential surface ($S_i$) of the rotational coupling part (12,20) to said height ($h_p$) of the permanent magnets (21) is at least 10:1.

3. Centrifugal blood pump comprising a housing (13) provided with at least one blood outlet (15') and at least one blood inlet (14) and closed in a liquid and gas-tight manner except at the at least one blood outlet (15') and at least one blood inlet (14), a rotatable pump rotor (15) arranged inside the housing (13) and provided with a number of ferromagnetic regions (17,18) distributed uniformly circumferentially in the pump rotor, an external drive motor (10) outside the housing (13) and means for magnetic coupling of the pump rotor (15) and the drive motor (10) to drive the pump rotor (15) rotatably, wherein said means for magnetic coupling of the pump rotor (15) and the drive motor (10) include a rotational coupling part (12,20) attached to the drive motor (10) to be rotatably driven thereby and arranged outside of the housing (13) and a number of permanent magnets (21) distributed uniformly around a circumference of the rotational coupling part (12,20) so that said pump rotor (15) is driven and rotationally stabilized by action of the permanent magnets (21) mounted on the rotational coupling part (12, 20) on the ferromagnetic regions (17,18) of the pump rotor (15), wherein said pump rotor (15) has an outer circumferential surface ($S_o$) having a radius ($r_o$) extending from a rotation axis (19) of the pump rotor (15) to said outer circumferential surface ($S_o$), said permanent magnets (21) have a height ($h_p$) in an axial direction and a ratio of said radius ($r_o$) of said outer circumferential surface ($S_o$) of the pump rotor (15) to said height ($h_p$) of the permanent magnets (21) is at least 10:1.

4. Centrifugal blood pump comprising a housing (13) provided with at least one blood outlet (15') and at least one blood inlet (14) and closed in a liquid and gas-tight manner except at the at least one blood outlet (15') and at least one blood inlet (14), a rotatable pump rotor (15) arranged inside the housing (13) and provided with a number of ferromagnetic regions (17,18) distributed uniformly circumferentially in the pump rotor, an external drive motor (10) outside the housing (13) and means for magnetic coupling of the pump rotor (15) and the drive motor (10) to drive the pump rotor (15) rotatably, wherein said means for magnetic coupling of the pump rotor (15) and the drive motor (10) include a rotational coupling part (12,20) attached to the drive motor (10) to be rotatably driven thereby and arranged outside of the housing (13) and a number of permanent magnets (21) distributed uniformly around a circumference of the rotational coupling part (12,20) so that said pump rotor (15) is driven and rotationally stabilized by action of the permanent magnets (21) mounted on the rotational coupling part (12, 20) on the ferromagnetic regions (17,18) of the pump rotor (15), wherein said rotational coupling part (12,20) has an inner circumferential surface ($S_i$) having a radius ($r_i$), said ferromagnetic regions (17,18) have a height ($h_f$) in an axial direction and a ratio of said radius ($r_o$) of said inner circumferential surface ($S_i$) of the rotational coupling part (12,20) to said height ($h_f$) of the ferromagnetic regions (17,18) is at least 10:1.

5. Centrifugal blood pump comprising a housing (13) provided with at least one blood outlet (15') and at least one blood inlet (14) and closed in a liquid and gas-tight manner except at the at least one blood outlet (15') and at least one blood inlet (14), a rotatable pump rotor (15) arranged inside the housing (13) and provided with a number of ferromagnetic regions (17,18) distributed uniformly circumferentially in the pump rotor, an external drive motor (10) outside the housing (13) and means for magnetic coupling of the pump rotor (15) and the drive motor (10) to drive the pump rotor (15) rotatably, wherein said means for magnetic coupling of the pump rotor (15) and the drive motor (10) include a rotational coupling part (12,20) attached to the drive motor (10) to be rotatably driven thereby and arranged outside of the housing (13) and a number of permanent magnets (21) distributed uniformly around a circumference of the rotational coupling part (12,20) so that said pump rotor (15) is driven and rotationally stabilized by action of the permanent magnets (21) mounted on the rotational coupling part (12, 20) on the ferromagnetic regions (17,18) of the pump rotor (15), wherein said pump rotor (15) has an outer circumferential surface ($S_o$) having a radius ($r_o$) extending from a rotation axis (19) of the pump rotor to said outer circumferential surface ($S_o$), said ferromagnetic regions (17,18) have a height ($h_f$) in an axial direction and a ratio of said radius ($r_o$) of said outer circumferential surface ($S_o$) of the pump rotor to said height ($h_f$) of the ferromagnetic regions (17,18) (21) is at least 10:1.

6. Centrifugal blood pump comprising a housing (13) provided with at least one blood outlet (15') and at least one blood inlet (14) and closed in a liquid and gas-tight manner except at the at least one blood outlet (15') and at least one blood inlet (14), a rotatable pump rotor (15) arranged inside the housing (13) and provided with a number of ferromagnetic regions (17,18) distributed uniformly circumferentially in the pump rotor, an external drive motor (10) outside the housing (13) and means for magnetic coupling of the pump rotor (15) and the drive motor (10) to drive the pump rotor (15) rotatably, wherein said means for magnetic coupling of the pump rotor (15) and the drive motor (10) include a rotational coupling part (12,20) attached to the drive motor (10) to be rotatably driven thereby and arranged outside of the housing (13) and a number of permanent magnets (21) distributed uniformly around a circumference of the rotational coupling part (12,20) so that said pump rotor (15) is driven and rotationally stabilized by action of the permanent magnets (21) mounted on the rotational coupling part (12, 20) on the ferromagnetic regions (17,18) of the pump rotor (15) and bearing means for mounting said rotor inside said housing (13) comprising a bearing post (23) centrally positioned inside said housing (13) and a bearing disk (24) of said pump rotor provided with a disk opening having a knife-like edge for engagement with said bearing post (23).

7. Centrifugal blood pump as defined in claim 6, wherein said rotational coupling part (12,20) includes a ring (20) and the permanent magnets (21) disposed on an interior circumferential side of the ring (20) and the ring (20) provides a magnetic ground bridge between the permanent magnets (21).

8. Centrifugal blood pump as defined in claim 6, wherein said ferromagnetic regions (17,18) are permanently magnetized.

9. Centrifugal blood pump as defined in claim 6, wherein the number of ferromagnetic regions (17,18) equals the number of permanent magnets (21) of the rotational coupling part (12,20).

10. Centrifugal blood pump as defined in claim 6, wherein the ferromagnetic regions (17,18) of the pump rotor (15) are provided in a disk-like rotor body driven part (15.1) and an impeller device comprising blade elements (16) is connected to the driven part (15.1) at least on one axial side of the rotor body driven part (15.1).

* * * * *